United States Patent
Goshima et al.

(10) Patent No.: US 10,293,518 B2
(45) Date of Patent: May 21, 2019

(54) FORMING MOLD, OPTICAL ELEMENT, AND METHOD FOR PRODUCING OPTICAL ELEMENT (71) Applicant: Konica Minolta, Inc., Tokyo (JP)

(72) Inventors: Takehiko Goshima, Kunitachi (JP); Yoshihiro Okumura, Toyohashi (JP)

(73) Assignee: KONICA MINOLTA, INC., Tokyo (JP)

( * ) Notice: Subject to any disclaimer, the term of this patent is extended or adjusted under 35 U.S.C. 154(b) by 19 days.

(21) Appl. No.: 15/738,489

(22) PCT Filed: Jun. 17, 2016

(86) PCT No.: PCT/JP2016/068117
§ 371 (c)(1),
(2) Date: Dec. 20, 2017

(87) PCT Pub. No.: WO2016/208509
PCT Pub. Date: Dec. 29, 2016

(65) Prior Publication Data
US 2018/0186037 A1 Jul. 5, 2018

(30) Foreign Application Priority Data
Jun. 25, 2015 (JP) .................... 2015-128170

(51) Int. Cl.
B29C 33/38 (2006.01)
G01N 21/64 (2006.01)
(Continued)

(52) U.S. Cl.
CPC .......... *B29C 33/3842* (2013.01); *B29C 33/38* (2013.01); *G01N 21/41* (2013.01);
(Continued)

(58) Field of Classification Search
CPC .... B29C 33/3842; B29C 33/38; G01N 21/41; G01N 21/64; G01N 21/648;
(Continued)

(56) References Cited

U.S. PATENT DOCUMENTS

2005/0191784 A1* 9/2005 Tsuruma .......... B29D 11/00365
438/70

FOREIGN PATENT DOCUMENTS

JP 2003194712 A 7/2003
JP 2006275535 A 10/2006
(Continued)

OTHER PUBLICATIONS

S. Stach, et al; Morphological features in aluminum nitride epilayers prepared by magnetron sputtering; Materials Science-Poland; vol. 33; No. 1; 2015; pp. 175-184.
(Continued)

*Primary Examiner* — Jamil Ahmed
(74) *Attorney, Agent, or Firm* — Lucas & Mercanti, LLP (57) ABSTRACT There is provided a forming mold 40 made on the basis of a standard more reliable than an average roughness of a surface of a metal film that generates surface plasmon resonance, the forming mold being capable of improving an S/N ratio of an optical element 20. A forming mold 40 for a substrate 21 of an optical element 20 used for measurements utilizing surface plasmon, wherein an Spc value of a molding surface 51t for transferring a shape onto a surface 21a of the substrate 21 on a side facing an object to be measured is equal to or less than 100 [1/mm].

15 Claims, 6 Drawing Sheets (51) Int. Cl.
*G01N 21/41* (2006.01)
*B29L 11/00* (2006.01)

(52) U.S. Cl.
CPC ........... *G01N 21/64* (2013.01); *G01N 21/648* (2013.01); *B29L 2011/00* (2013.01)

(58) Field of Classification Search
CPC ..... B29L 2011/00; C23C 14/08; C23C 14/34; C12Q 1/00; G01J 3/28; H01L 23/495; H01L 21/50; H01L 21/60; G02F 1/1337; G02F 1/1339
See application file for complete search history.

(56) References Cited

FOREIGN PATENT DOCUMENTS

| | | | |
|---|---|---|---|
| JP | 2007078451 A | 3/2007 | |
| JP | 2009230811 A | 10/2009 | |
| JP | 2011184706 A | 9/2011 | |
| JP | 2014140970 A | 8/2014 | |

OTHER PUBLICATIONS

International Search Report dated Aug. 30, 2016 for PCT/JP2016/068117.
Extended European Search Report dated May 9, 2018 from corresponding European Application No. 16814280.0.

* cited by examiner

FORMING MOLD, OPTICAL ELEMENT, AND METHOD FOR PRODUCING OPTICAL ELEMENT

CROSS REFERENCE TO RELATED APPLICATION

This Application is a 371 of PCT/JP2016/068117 filed on Jun. 17, 2016, which, in turn, claimed the priority of Japanese Patent Application No. JP 2015-128170 filed on Jun. 25, 2015, both applications are incorporated herein by reference.

TECHNOLOGICAL FIELD

The present invention relates to a forming mold for forming the substrate of an optical element used for a surface plasmon resonance sensor, such an optical element, and a method for producing such an optical element.

BACKGROUND

In recent years, in the fields of a biosensor etc., various sensors using surface plasmon resonance have been put in practical use. The examples of a sensor using Surface Plasmon-field enhanced Fluorescence Spectroscopy (SPFS) include one, wherein a metal film is formed via a thin substrate on an inclined plane of a prism, and the metal thin film is irradiated with a laser beam from a back side, which is the inner side of the prism, to generate surface plasmon resonance and an enhanced electric field at the surface of the metal thin film (see Patent Literature 1). Note that this Patent Literature 1 describes that the average roughness Ra of the surface of the metal film is set to be equal to or less than 4 nm.

Moreover, the examples of a scanning near-field optical microscope utilizing surface plasmon resonance include the one, wherein a metal thin film is formed via a thin substrate on an inclined plane of a prism, and the metal thin film is irradiated with a laser beam from a back side, which is the inner side of the prism, to generate surface plasmon resonance at the surface of the metal thin film, thereby detecting a proximity light with an opposed probe (see Patent Literature 2). Note that this Patent Literature 2 describes that the average roughness of the surface of the metal thin film is desirably set to be equal to or less than 0.1 nm.

Other than the above, the examples of a surface plasmon resonance apparatus, which causes a light beam to enter the opposite side of a sample of a metal film and detects an attenuation state of a totally reflected light thereof, include the one having an incident face and emitting face provided in the bottom portion of a container-like chip to be measured and having a metal film formed in the upper face of the bottom portion (see Patent Literature 3). Note that this Patent Literature 3 does not describe the surface roughness of a metal film.

In an apparatuses utilizing the surface plasmon resonance phenomena as described above, the metal thin film of a sensor might be desirably smooth, but according to the study of the present inventor, it turned out that a reduction of the average roughness of the metal thin film does not necessarily result in an improvement of the S/N ratio.

CITATION LIST

Patent Literature

Patent Literature 1: Japanese Patent Laid-Open No. 2011-184706

Patent Literature 2: Japanese Patent Laid-Open No. 2007-78451

Patent Literature 3: Japanese Patent Laid-Open No. 2003-194712

SUMMARY

The present invention has been made in view of the above-described background art, and has an object to provide a forming mold made on the basis of a standard more reliable than the average roughness of a surface of a metal film that generates surface plasmon resonance, the forming mold being capable of improving the S/N ratio of an optical element.

Moreover, it is an object of the present invention to provide an optical element capable of suppressing the generation of a scattered light in a metal film and a method for producing the same.

In order to achieve the above-described objects, a forming mold according to the present invention is the forming mold for the substrate of an optical element used for the measurement utilizing surface plasmon, wherein an Spc value of a molding surface for transferring a shape onto the surface of a substrate on a side facing an object to be measured is equal to or less than 100 [in the unit of 1/mm]. Here, the Spc value is an indicator for evaluating a microscopic uneven state in a target surface, and is an arithmetic average of principal curvatures of mountain peaks inside an observation area.

In the above-described forming mold, since the Spc value of a molding surface is equal to or less than 100 [1/mm], the state of the surface of a substrate, on a side facing an object to be measured, obtained by transferring the molding surface can be made smooth to the extent that the generation of a scattering light at a metal film to be formed on this surface can be appropriately suppressed. Thus, an optical element obtained from the substrate can be made precise, and the S/N ratio in the measurement utilizing the surface plasmon resonance phenomenon such as Surface Plasmon-field enhanced Fluorescence Spectroscopy can be improved. Thus, the control parameter of a noise component such as a scattering light due to the forming mold of an optical element might be able to be clarified.

In order to achieve the above-described objects, the optical element according to the present invention is an optical element used for the measurement utilizing surface plasmon, and the Spc value of a surface to be irradiated on the back side of a sensor face is equal to or less than 100 [1/mm].

In the above-described optical element, since the Spc value of the surface to be irradiated is equal to or less than 100 [1/mm], the state of this surface to be irradiated becomes smooth to the extent that the generation of a scattering light at a metal film constituting this surface to be irradiated can be appropriately suppressed. Thus, the S/N ratio in the measurement utilizing the surface plasmon resonance phenomenon such as Surface Plasmon-field enhanced Fluorescence Spectroscopy can be improved.

In order to achieve the above-described objects, a method for producing an optical element according to the present invention is the one used for the measurement utilizing surface plasmon, wherein a substrate of the optical element is formed by using a forming mold, and an Spc value of a molding surface for transferring a shape onto a surface of a substrate on a side facing an object to be measured of the forming mold is equal to or greater than 30 [1/mm] and equal to or less than 100 [1/mm].

According to the above-described producing method, since the Spc value of a molding surface is equal to or less than 100 [1/mm], the state of a surface of a substrate, on a side facing an object to be measured, obtained by transferring the molding surface can be made smooth to the extent that the generation of a scattering light at a metal film to be formed on this surface can be appropriately suppressed. Thus, the S/N ratio in the measurement utilizing the surface plasmon resonance phenomenon such as Surface Plasmonfield enhanced Fluorescence Spectroscopy can be improved. Furthermore, since the Spc value of a molding surface is equal to or greater than 30 [1/mm], the molding surface can be relatively easily machined and the detection of a plasmon resonance angle can be facilitated.

BRIEF DESCRIPTION OF DRAWINGS

FIG. 1A is a cross sectional view illustrating a forming mold of an embodiment, while

DETAILED DESCRIPTION OF EMBODIMENTS

Embodiments

A forming mold, an optical element, and a method for producing the same according to an embodiment of the present invention will be explained with reference to the drawings.

Figure 1A:
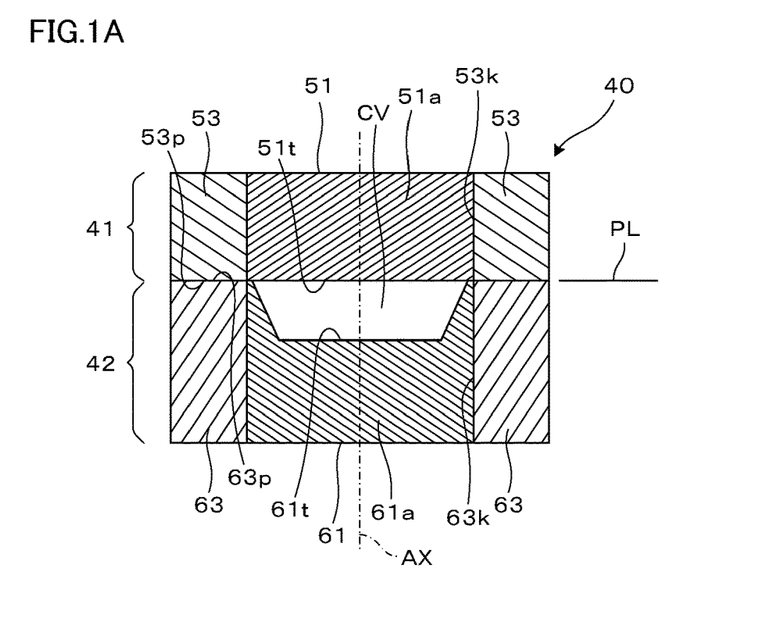

A forming mold 40 of this embodiment illustrated in FIG. 1A is used for injection molding of a thermoplastic resin. The forming mold 40 includes a fixed mold 41 and a movable mold 42, and the both molds 41 and 42 are openable and closable at a parting line PL as a boundary. A cavity CV which is a mold space sandwiched by the fixed mold 41 and movable mold 42 corresponds to the shape of a resin molded article MP (see, FIG. 2C etc.) described later.

Figure 2A:
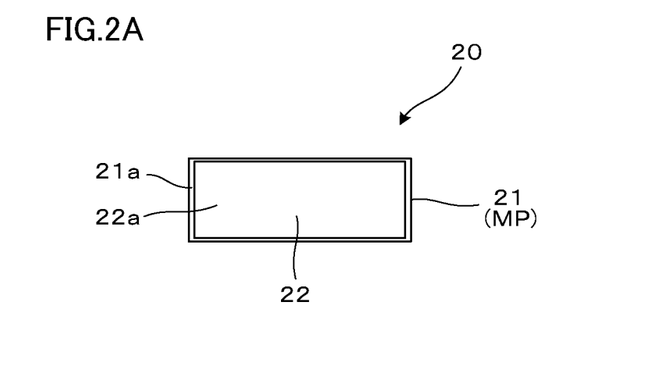
FIGS. 2A, 2B and 2C are a front side view, lateral side cross sectional view, and back side view of an optical element of an embodiment.
Figure 2B:
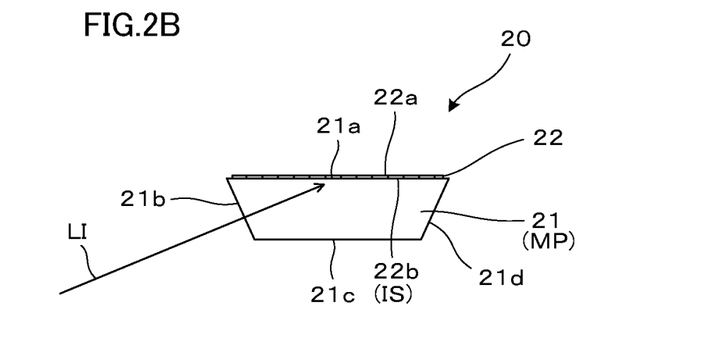
Figure 2C:
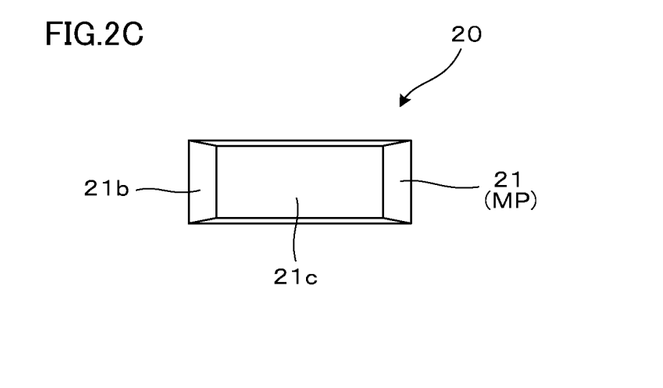

FIGS. 2A to 2C are the schematic front side view, lateral side cross sectional view, and back side view of an optical element 20 obtained from the resin molded article MP which is formed with the forming mold 40 of FIG. 1A. As illustrated in the views, the optical element 20 is a strip-like flat plate, and includes a substrate 21 made of an optically-transparent resin, and a metal film 22 covering a surface 21a of the substrate 21 on a side facing an object to be measured and forming a sensor face 22a.

The substrate 21 of the optical element 20 is formed from a resin, for example such as acrylic (PMMA), cycloolefin polymer (COP) or a cycloolefin copolymer (COC). By forming the substrate 21 from a resin, the optical element 20 can be fabricated at a relatively low cost. The surface 21a of the substrate 21 on a side facing an object to be measured is a smooth and mirror-like flat plane. This surface 21a is covered with the metal film 22 described later. That is, the face obtained by reversing the shape of the surface 21a corresponds to a rear surface 22b of the metal film 22, i.e., a surface to be irradiated IS which is caused to totally reflect an irradiation light LI. The surface 21a does not directly have a restriction on the Spc value related to the microscopic uneven state, but indirectly has a restriction on the microscopic uneven state due to a restriction on the Spc value of the surface to be irradiated IS. Accordingly, by forming the substrate 21 by molding using the forming mold 40, the state of the microscopic unevenness of the inner surface of the metal film 22 can be simply evaluated with the molding surface 51t (see FIG. 1A) of the forming mold 40. An inclined plane 21b provided at one end of the substrate 21 is a surface which causes the irradiation light LI emitted from a non-illustrated light source to enter the inside of the optical element 20. The inclined plane 21b is set, from the viewpoint of not allowing the irradiation light LI incident thereupon to be significantly scattered, to a flat plane having the value of the surface roughness equal to or less than a predetermined value. A remaining inclined surface 21d of the substrate 21 does not have an optical function in particular, but can be set to a surface which causes the irradiation light LI to be emitted to the outside of the optical element 20.

The metal film 22 is formed so as to substantially cover the whole surface 21a of the substrate 21 on a side facing an object to be measured. The metal film 22 is formed, for example, from either one of gold, silver, aluminum, platinum, copper, titanium, and chromium, or from an alloy containing two or more thereof or the like. Such a metal film 22 is capable of relatively efficiently generating surface plasmon resonance. The metal film 22 is formed by using a film-forming technique, such as sputtering, vapor deposition, or ion plating. The thickness of the metal film 22 is on the order from 20 nm to 100 nm. The surface of the metal film 22, i.e., the sensor face 22a, is a flat plane substantially following the surface 21a of the substrate 21.

Note that the rear surface 22b of the metal film 22 covers the surface 21a of the substrate 21, and functions as the surface to be irradiated IS. That is, the rear surface 22b of the metal film 22 or surface to be irradiated IS has a shape obtained by reversing the surface 21a of the substrate 21. In the rear surface 22b of the metal film 22 or surface to be irradiated IS, the Spc value related to the microscopic uneven state of a surface to be described in detail later is set to be equal to or greater than 28 [1/mm] and equal to or less than 100 [1/mm]. However, this rear surface 22b or surface to be irradiated IS has a restriction on the Spc value, but does not particularly have a restriction on the value of the surface roughness (specifically, Ra (arithmetic average roughness), Rq (root-mean-square height), Rz (maximum height), or Rt (maximum cross section height)). Note that, even if the Spc value of the surface to be irradiated IS is equal to or greater than 28 [1/mm] but if the Spc value of the above-described molding surface 51t for forming this surface to be irradiated IS is equal to or greater than 30 [1/mm], this condition is within the scope of the present invention.

The optical element 20 includes: the optically-transparent substrate 21; and the metal film 22 which covers the surface 21a of this substrate 21 on a side facing an object to be measured, functions as the surface to be irradiated IS, and has the sensor face 22a on the front side. Therefore, when light is caused to enter the surface to be irradiated IS (i.e., the rear surface 22b of the metal film 22) at a predetermined angle from the inside of the substrate 21, surface plasmon resonance can be efficiently generated in the metal film 22.

Returning to FIG. 1A, the fixed mold 41 includes a core section 51 and a peripheral mold 53. Here, the core section 51 is arranged facing a core section 61 of the movable mold 42 in order to form the cavity CV. The peripheral mold 53 is a mold member which holds the core section 51 from therearound.

The core section 51 is formed from a carbon steel, an aluminum alloy, a copper alloy, a cemented carbide, a titanium alloy, or the like. At a tip part of the core section 51, the molding surface 51t is provided in order to define the cavity CV. The molding surface 51t is a smooth and mirror-like flat plane, and is a transfer surface for forming the surface 21a of the substrate 21 of the optical element 20. The Spc value related to the microscopic uneven state of the molding surface 51t is equal to or greater than 30 [1/mm] and equal to or less than 100 [1/mm]. However, the molding surface 51t does not particularly have a restriction on the value of the surface roughness (specifically, Ra (arithmetic average roughness), Rq (root-mean-square height), Rz (maximum height), or Rt (maximum cross section height)). Since the Spc value of the molding surface 51t is equal to or greater than 30 [1/mm], the restriction on the microscopic uneven state is not severe and therefore the molding surface 51t can be relatively easily machined. Moreover, if the Spc value of the molding surface 51t is equal to or greater than 30 [1/mm], a scattering light having a level equal to or greater than a certain level is generated in the metal film 22, so the detection of a plasmon resonance angle can be facilitated.

As described above, the core section 51 transfers a shape onto the surface 21a of the substrate 21 on a side facing an object to be measured and is a target for evaluating the Spc value. By using the core section 51, the molding surface 51t specific to the surface 21a of the substrate 21 on a side facing an object to be measured can be easily formed and the shape accuracy of the surface 21a of the substrate 21 on a side facing an object to be measured can be easily improved.

Here, the Spc value will be explained. The Spc value means an arithmetic average curvature of mountain or protrusion peaks (arithmetic mean peak curvature) defined by ISO25178, and is the value obtained by evaluating the microscopic uneven state of a target surface as an average value of the curvatures of mountain peaks. The Spc value is theoretically given by Formula below.

$$Spc = -\frac{1}{2} \cdot \frac{1}{n} \sum_{k=1}^{n} \left( \frac{\partial^2 z(x, y)}{\partial z^2} + \frac{\partial^2 z(x, y)}{\partial y^2} \right)$$

Herein, Z (x, y) is the height at a position (x, y) of a target surface and n is the number of mountain peaks of the target surface.

In the case of measuring the Spc value of an actually machined surface, a three-dimensional shape of a target surface is measured, for example, by using a confocal laser scanning microscope, a mountain peak is extracted from the three-dimensional shape obtained in this manner, and an arithmetic average of the principal curvatures is calculated for the respective mountain peaks, thereby enabling calculation of an Spc value. For example, in the case of calculating the Spc value of the molding surface 51t of the core section 51, the resolutions of the position and/or height are set to be equal to or less than the order from 1 nm to 10 nm in consideration of reproducibility etc.

The Spc value of the molding surface 51t is measured by directly measuring this molding surface 51t as described above, but by negatively transferring the surface 21a of the substrate 21, which is a molding article obtained from the molding surface 51t, onto a UV curing resin etc., the Spc value of the molding surface 51t can also be obtained from this negative transfer-surface.

When the Spc value of the molding surface 51t is equal to or less than 100 [1/mm], the state of the surface 21a of the substrate 21, on a side facing an object to be measured, obtained by transferring the molding surface 51t can be made smooth to the extent that the generation of a scattering light at the metal film 22 to be formed on this surface 21a can be appropriately suppressed. Here, a scattering light results in a noise component in detecting the fluorescence from a material to be inspected. That is, by controlling the surface state of the molding surface 51t with the Spc value, the surface state of the surface 21a of the substrate 21 can be controlled, and the generation of a scattering light at the metal film 22 formed on the surface 21a can be appropriately suppressed. Thus, an increase in the accuracy of the optical elements 20 obtained from the substrate 21 can be achieved, and the S/N ratio in the measurement utilizing Surface Plasmon-field enhanced Fluorescence Spectroscopy can be improved. On the other hand, when the Spc value of the molding surface 51t is equal to or greater than 30 [1/mm], the restriction on the microscopic uneven state is not severe and therefore the molding surface 51t can be relatively easily machined. Moreover, if the Spc value of the molding surface 51t is equal to or greater than 30 [1/mm], a scattering light of a level equal to or greater than a certain level is generated in the metal film 22, so the detection of a plasmon resonance angle for increasing a signal level can be facilitated.

Note that the Spc value of the molding surface 51t is more preferably equal to or greater than 40 [1/mm] and equal to or less than 60 [1/mm]. If the Spc value of the molding surface 51t is equal to or less than 60 [1/mm], the S/N ratio will further improve, and if the Spc value is equal to or greater than 40 [1/mm], the molding surface 51t can be more easily machined and the plasmon resonance angle can be also more easily detected.

The core section 51 includes a body portion 51a. The body portion 51a is formed, for example, from a material containing either one or more of a carbon steel, an aluminum alloy, a copper alloy, a cemented carbide, and a titanium alloy. The examples of the carbon steel include a stainless steel, such as STAVAX, HPM38, and HPM38s. The examples of the cemented carbide include a stainless steel, such as a micro alloy F or Anviloy, other than a tungsten carbide. In this case, the shape of the molding surface 51t which is a transfer surface can be made highly rigid, reproducible, and accurate, and the durability of the molding surface 51t against heat, wear, etc. can be improved. The leading end surface of the body portion 51a is machined into the molding surface 51t. Note that, a release film formed from, for example, a silane coupling agent etc., can also be added to the surface of the molding surface 51t. When a release film has been formed, the surface of the release film might be regarded as the molding surface 51t in a strict sense. However, since the release film is extremely thin, also in this case the Spc value of the leading end surface of the body portion 51a is adapted to be equal to or greater than 30 [1/mm] and equal to or less than 100 [1/mm].

Other than the above, a cylindrical through-hole 53k, which supports the core section 51 thereinside by being inserted therein, is formed in the peripheral mold 53. Moreover, the peripheral mold 53 has an end face 53p forming the parting line PL.

The movable mold 42 includes the core section 61 and a peripheral mold 63. The movable mold 42 is movable along an axis AX, and performs closing and opening operations on the fixed mold 41. In the movable mold 42, the core section 61 is arranged facing the core section 51 of the fixed mold 41 in order to form the cavity CV. The peripheral mold 63 is a mold member which holds the core section 61 from therearound.

At a tip part of the core section 61, a molding surface 61t is provided in order to define the cavity CV. The molding surface 61t is a recessed face having a uniform depth on the central side, and is the transfer surface which forms the inclined plane 21b, rear surface 21c, etc. of the substrate 21 of the optical element 20. The surface areas corresponding to the inclined plane 21b and rear surface 21c of the optical element 20 of the molding surface 61t have a surface roughness equal to or less than the order of the surface roughness required for these inclined plane 21b and rear surface 21c.

The core section 61 includes a body portion 61a as with the core section 51 of the fixed mold 41. The material of the body portion 61a is the same as that of the body portion 51a constituting the core section 51 of the fixed mold 41, so the explanation thereof is omitted. Note that a release film can also be added to the surface of the body portion 61a.

Other than the above, a cylindrical through-hole 63k, which supports the core section 61 thereinside by being inserted therein, is formed in the peripheral mold 63. Moreover, the peripheral mold 63 has an end face 63p forming the parting line PL. Furthermore, in the peripheral mold 63, a runner recess and a gate recess, though illustration thereof is omitted, are provided in order to introduce a melting resin into the cavity CV.

Figure 1B:
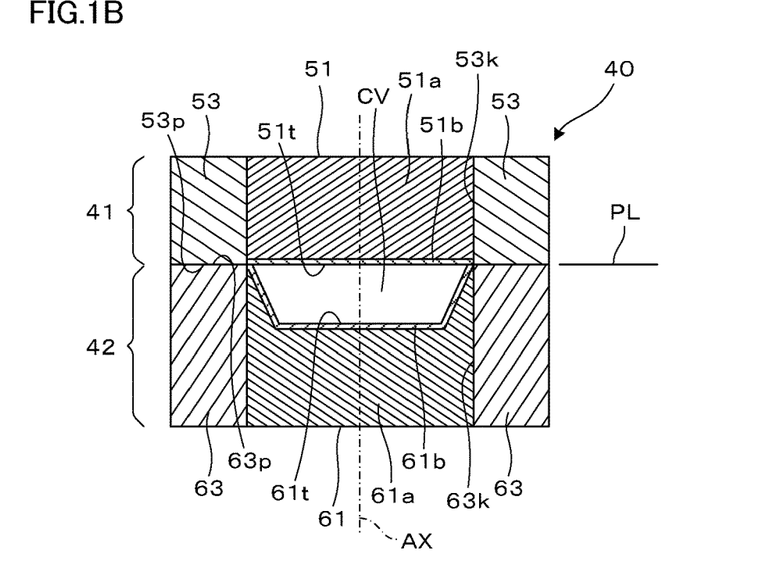
FIG. 1B illustrates a modified example of the forming mold of FIG. 1A.

FIG. 1B illustrates a modified example of the forming mold 40 illustrated in FIG. 1A. In this case, the core section 51 on the fixed mold 41 side includes a transfer-surface machined layer 51b on the tip side of the body portion 51a. The leading end surface of the body portion 51a is a substantially flat plane corresponding to the molding surface 51t. The transfer-surface machined layer 51b is a nickel-P plated layer (nickel phosphorous-plated layer) which is formed by using electroless nickel plating, for example, and has a thickness on the order from several tens of micrometers to several millimeters. The transfer-surface machined layer 51b is provided so as to cover a tip of the body portion 51a in order to improve machinability. The molding surface 51t which is the surface of the transfer-surface machined layer 51b is machined into an accurate optical transfer-surface, and the Spc value related to the microscopic uneven state is equal to or greater than 30 [1/mm] and equal to or less than 100 [1/mm].

Note that, a thin protective film formed from a material, for example such as chromium (Cr), chrome oxide ($Cr_2O_3$), alumina ($Al_2O_3$), and/or silicon carbide (SiC), can be added to the surface of the transfer-surface machined layer 51b. Furthermore, a thin release film formed from, for example, a silane coupling agent etc. can be added to the surface of such a protective film. When a protective film as described above is formed, the surface of the protective film serves as the molding surface 51t in a strict sense, and the Spc value related to the microscopic uneven state is set to be equal to or greater than 30 [1/mm] and equal to or less than 100 [1/mm].

The core section 61 of the movable mold 42 includes the body portion 61a and transfer-surface machined layer 61b as with the core section 51 of the fixed mold 41. The materials of the body portion 61a and transfer-surface machined layer 61b are the same as those of the body portion 51a and transfer-surface machined layer 51b constituting the core section 51 of the fixed mold 41, so the explanation thereof is omitted. Note that a thin protective film can be added to the surface of the transfer-surface machined layer 61b and a thin release film can also be added to the surface of such a protective film.

Hereinafter, a measurement apparatus incorporating the optical element 20 illustrated in FIG. 2B etc. will be explained with reference to FIG. 3.

An illustrated measurement apparatus 70 is an apparatus utilizing Surface Plasmon-field enhanced Fluorescence Spectroscopy. The measurement apparatus 70 includes: a sample cell 71 having the optical element 20 as a surface plasmon resonance sensor attached thereto; a photodetector 72 which detects the fluorescence from the sample cell 71; a laser light source 73 which causes the irradiation light LI to enter the optical element 20; and a control unit 79 which integrally controls these operations.

The sample cell 71 includes a channel to be inspected 71a, a pair of ports 71b, 71c, and a detection window 71e. The channel to be inspected 71a is space for circulating a material to be inspected, and is like a flat thin layer. The sample cell 71 makes the optical element 20 detachable or exchangeable by a holding mechanism, the detailed explanation of which is omitted.

Figure 4:
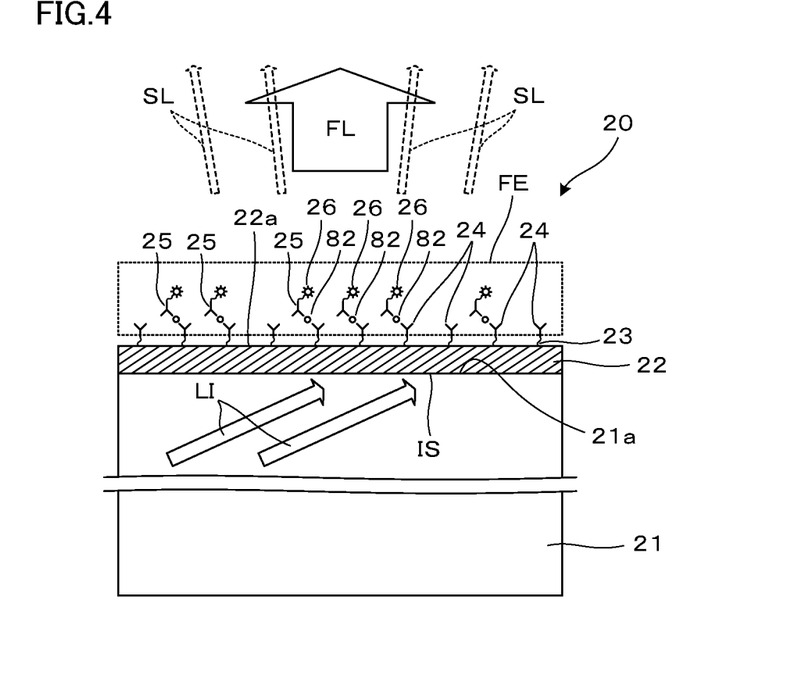
FIG. 4 is an expanded cross sectional view of surroundings of a sensor face of the optical element.

As illustrated in FIG. 4, to the sensor face 22a on the front side of the metal film 22 provided in the optical element 20, an antibody 24 is fixed in advance by utilizing a support layer 23 consisted of SAM and/or polymer. The antibody 24 is for capturing a target material 82, and is selected in accordance with the target material 82. The target material 82 corresponds to an antigen serving as an indicator of a certain sickness, for example.

Returning to FIG. 3, the photodetector 72 is configured by a photomultiplier tube, a CCD, etc. and detects, through the detection window 71e, weak fluorescence inside the channel to be inspected 71a as a signal. Note that a filter corresponding to an emission wavelength of a target fluorescent label can be added to the photodetector 72.

The laser light source 73 generates the irradiation light LI of a specified wavelength in a visible to infrared wavelength region, and causes the same to enter the surface to be irradiated IS of the optical element 20. The irradiation light LI is a P-polarized light, for example. The laser light source 73 is accompanied by an angle adjustment section 74 so as to be able to adjust an incident angle $\theta$ with a normal NO of the surface to be irradiated IS of the irradiation light LI set as a reference. By adjusting the incident angle $\theta$ incident upon the surface to be irradiated IS of the irradiation light LI in the state where the sample cell 71 is empty for example, the incident angle $\theta$ when the intensity of scattering light SL detected by the photodetector 72 (see FIG. 4) becomes the maximum, i.e., a plasmon resonance angle, can be determined. Here, it is considered that the plasmon resonance angle is a state where the surface plasmon resonance is being efficiently generated by the irradiation light LI in the surface of the metal film 22 of the optical element 20, and consequently the scattering light SL emitted from the sensor face 22a of the metal film 22 also becomes the maximum.

The control unit 79 causes a dispenser (not shown), which supplies the sample cell 71 with an analyte of the material to be inspected or the like, to operate at a desired timing.

Moreover, the control unit 79 causes, after supplying the sample cell 71 with an analyte etc., the laser light source 73 to operate and cause the irradiation light LI to enter the surface to be irradiated IS of the optical element 20. In this case, the control unit 79 processes a detection signal from the photodetector 72 to determine the presence or absence of the target material 82.

Hereinafter, a specific measurement will be explained. First, an analyte is fed into the channel to be inspected 71a of the sample cell 71. Then, as illustrated in FIG. 4, the target material 82 inside the analyte is captured by the antibody 24 on the sensor face 22a due to an antigen/antibody reaction. Subsequently, if a labeled liquid containing a fluorescence-labeled antibody 25 is fed after washing, the fluorescence-labeled antibody 25 is fixed to the target material 82. Subsequently, in the state after washing, if the surface to be irradiated IS of the optical element 20 is irradiated with the irradiation light LI, surface plasmon resonance occurs on the sensor face 22a side of the metal film 22 and an enhanced electric field FE is generated in a periphery thereof. A fluorescent material 26 of the antibody 25 is excited by this electric field FE to generate fluorescence FL. This fluorescence FL is detected as a fluorescence signal or a signal by the photodetector 72.

Here, since the electric field FE generated by surface plasmon resonance is enhanced, the light quantity of the fluorescence FL emitted from the fluorescent material 26 becomes several times to tens of times larger as compared with the light quantity when the fluorescent material 26 is caused to emit light by using another approach. Therefore, the target material 82 can be detected from an analyte containing only quite a small amount of the target material 82, and the sickness can be detected at an early stage even for a patient who exhibits little symptom of a sickness.

Examples

Hereinafter, specific Examples of the forming mold and optical element will be explained. First, the raw material of the core section 51 of the fixed mold 41 is machined to form the molding surface 51t at an end portion thereof. In forming the molding surface 51t, grinding was performed first and then mirror polishing was performed. As the material of the core section 51, STAVAX (trademark) or Anviloy (trademark) was used. In mirror polishing as the finishing up of the molding surface 51t, two types of polishing, i.e., normal-polishing and super-polishing, were performed by using a lap grinder. The difference between normal-polishing and super-polishing is an abrasive, and an abrasive B for super-polishing is the one obtained by improving an abrasive A of normal-polishing so as to be able to form a smoother surface. For a large number of core sections 51 obtained by changing the conditions in this manner, the surface shape was measured by using an objective lens ×50 in VX-250 manufactured by Keyence Corporation. Table 1 below summarizes the material of the mirror surface of the core section 51 (i.e., prototype core sections Y, Z, A to F), the polishing methods of the mirror surface, the surface roughness (Ra (arithmetic average roughness), Rq (root-mean-square height), Rz (maximum height) or Rt (maximum cross-section height)), and the Spc values.

Note that, in the determination column of manufacturability, the manufacturing cost is focused and indicated as follows: the core section 51 in which the Spc value is equal to or greater than 40 [1/mm] was relatively easily fabricated ("single-circle" mark), the core section 51 in which the Spc value is less than 40 [1/mm] and equal to or greater than 30 [1/mm] was not so easily fabricated ("triangle" mark), and the core section 51 in which the Spc value is less than 30 [1/mm] was not easily fabricated.

TABLE 1

| MOLD | MIRROR-SURFACE CORE MATERIAL | MIRROR POLISHING METHOD | Ra nm | Rq nm | Rz nm | Rt nm | Spc 1/mm | DETERMINATION OF MANUFACTURABILITY (MANUFACTURING COST) |
|---|---|---|---|---|---|---|---|---|
| CORE SECTION Y | STAVAX | NORMAL-POLISHING | 1.20 | 1.52 | 14.13 | 17.71 | 256.2 | ○ |
| CORE SECTION Z | ANVILOY | SUPER-POLISHING | 0.83 | 1.11 | 11.78 | 13.42 | 91.6 | ○ |
| CORE SECTION A | STAVAX | SUPER-POLISHING | 0.66 | 0.85 | 6.99 | 8.83 | 80.8 | ○ |
| CORE SECTION B | STAVAX | SUPER-POLISHING | 0.75 | 0.96 | 7.58 | 8.27 | 56.4 | ○ |
| CORE SECTION C | STAVAX | SUPER-POLISHING | 0.32 | 0.41 | 3.68 | 4.33 | 49.3 | ○ |
| CORE SECTION D | STAVAX | SUPER-POLISHING | 0.32 | 0.40 | 3.26 | 3.72 | 49.8 | ○ |
| CORE SECTION E | STAVAX | SUPER-POLISHING | 0.73 | 0.96 | 10.61 | 17.00 | 49.7 | ○ |
| CORE SECTION F | STAVAX | SUPER-POLISHING | 0.36 | 0.43 | 5.28 | 6.11 | 31.3 | Δ |

Utilizing each core section 51 obtained as described above, multiple types of substrates 21 were formed as the molded article by injection molding. The resin material used for molding is cycloolefin polymer E48R. For confirmation, a replica (the negative transfer object of a molded article) for the surface 21a of the substrate 21 was formed by transferring a shape by using a UV curing resin, and the Spc value of this replica was measured under the same conditions as the core section 51. This Spc value corresponds to the Spc value of the surface to be irradiated IS of the rear surface of the metal film 22.

In parallel to this, the surface 21a of each substrate 21 was coated with the gold metal film 22 to fabricate the optical element 20. A magnetron sputtering apparatus was used for deposition of the metal film 22. All the conditions (discharge voltage, gas flow rate, deposition rate, magnet rotation speed, etc.) of depositing gold (Au) onto each substrate 21 were the same. Such optical elements 20 each was set to the measurement apparatus 70 as illustrated in FIG. 3, the surface to be irradiated IS inside the optical element 20 was irradiated with the irradiation light LI, the incident angle of the irradiation light LI was adjusted so that the scattering light SL becomes the maximum, and the light quantity (i.e., scattered light quantity) of the scattering light SL at this time was recorded. Moreover, the antibody 24 was fixed to the sensor face 22a of the optical element 20, which was then attached to the sample cell 71, and after a known analyte was fed into this sample cell 71, a labeled liquid containing the fluorescence-labeled antibody 25 was fed thereinto. Subsequently, the surface to be irradiated IS inside the optical element 20 was irradiated with the irradiation light LI to observe the generation of fluorescence. Table 2 below summarizes the results thereof.

TABLE 2

| MOLDED ARTICLE | MOLDED ARTICLE RESIN MATERIAL | UV CURING RESIN MOLDED ARTICLE TRANSFER Spc 1/mm | SCATTERED LIGHT QUANTITY OF GOLD-COATED OPTICAL ELEMENT NORMALIZED, WITH CORE SECTION E SET AS ONE | DETERMINATION OF PERFORMANCE (S/N RATIO) |
|---|---|---|---|---|
| SUBSTRATE Y | E48R | 250.7 | 31.8 | X |
| SUBSTRATE Z | E48R | 90.1 | 9 | ○ |
| SUBSTRATE A | E48R | 79.5 | 5.6 | ○ |
| SUBSTRATE B | E48R | 53.6 | 2.5 | ⊚ |
| SUBSTRATE C | E48R | 46.4 | 1.6 | ⊚ |
| SUBSTRATE D | E48R | 46.6 | 1.8 | ⊚ |
| SUBSTRATE E | E48R | 46.2 | 1 | ⊚ |
| SUBSTRATE F | E48R | 28.7 | 0.1 | ⊚ |

In Table 2 above, for the scattered light quantity (light quantity of the scattering light SL), the scattered light quantity obtained with the optical element E fabricated from the substrate E fabricated with a core section E was set as a reference, and the scattered light quantity of each of optical elements A to D, F, Y, and Z obtained from each of substrates A to D, F, Y, and Z fabricated by the other cores A to D, F, Y, and Z was normalized. Moreover, in the determination column of the performance (S/N ratio), a case where the target material 82 could be detected with a sufficient sensitivity is indicated by a "double-circle" mark, a case where the target material 82 could not be clearly detected is indicated by a "christcross" mark, and a case where the target material 82 could be barely detected although the noise level was high is indicated by a "single-circle."

Figure 5A:
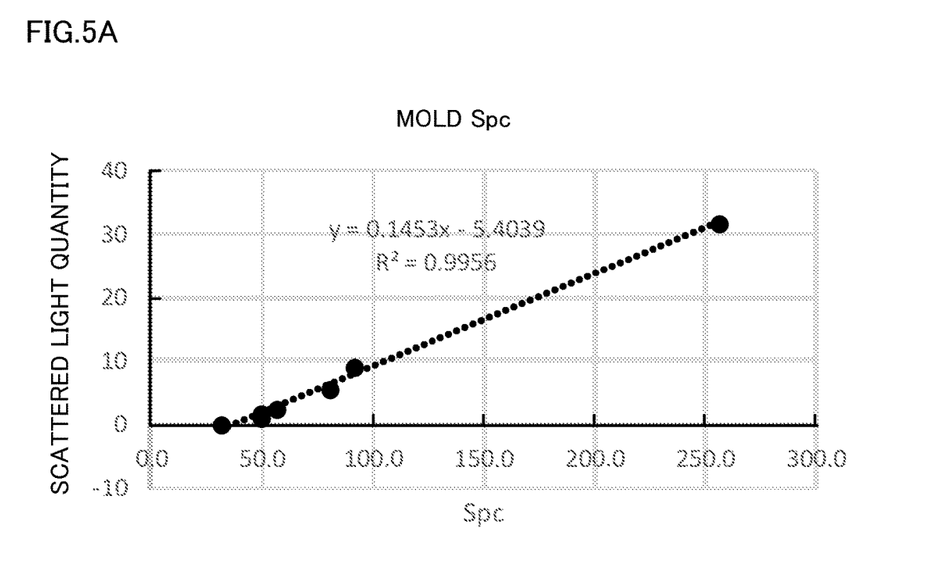
FIGS. 5A and 5B are the graphs each illustrating a relationship between an Spc value of a molding surface and a scattered light quantity.
Figure 5B:
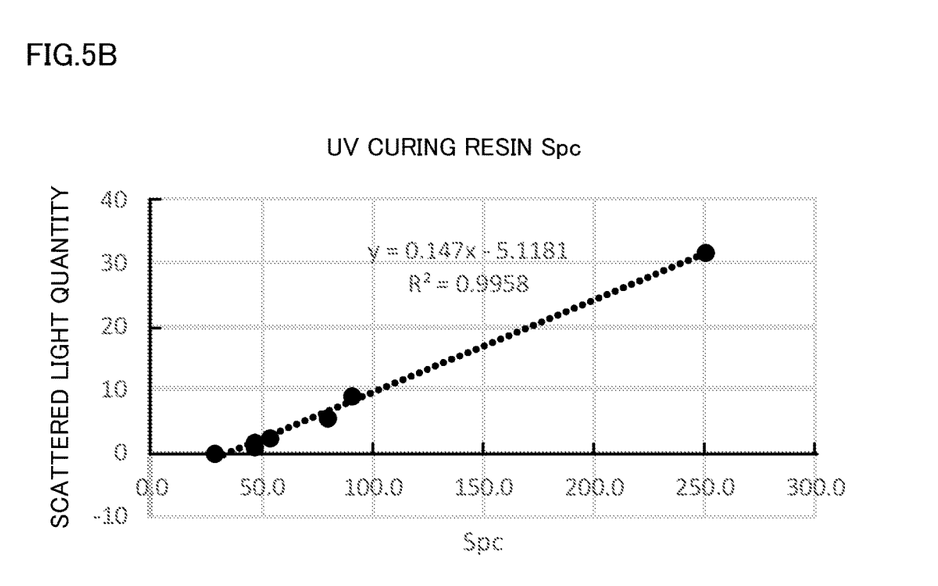
Figure 6A:
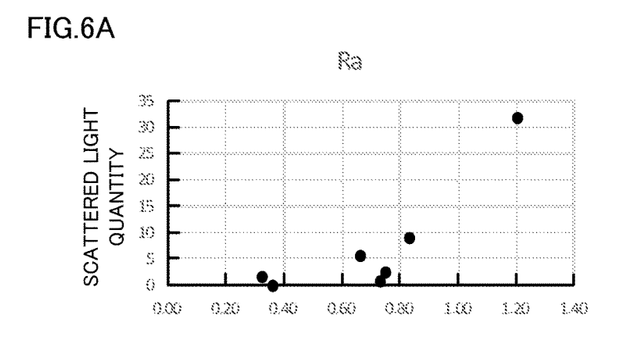
FIGS. 6A to 6D are the graphs each illustrating a relationship between the surface roughness (Ra, Rq, Rz, and Rt) of a molding surface and a scattered light quantity.
Figure 6B:
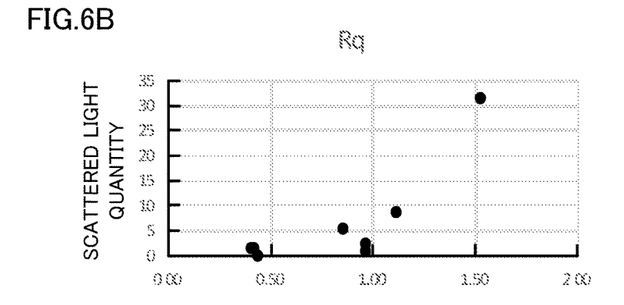
Figure 6C:
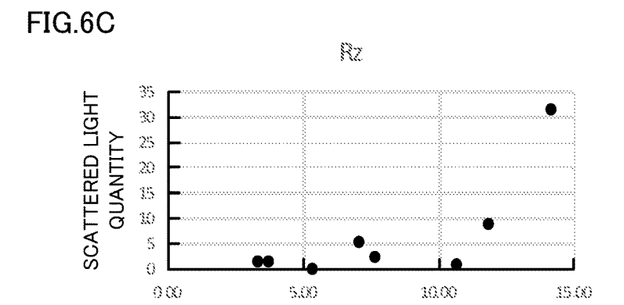
Figure 6D:
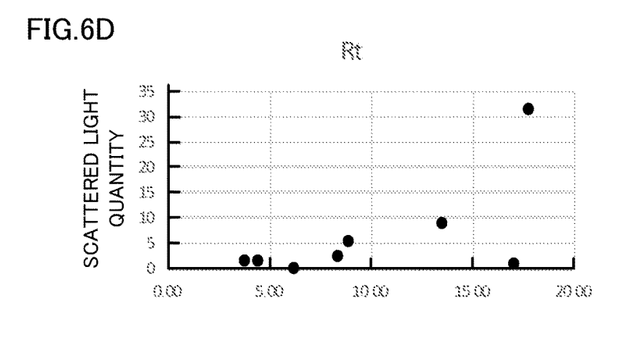

FIG. 5A is a graph of a relationship between the Spc value of the molding surface 51t of each of the core sections 51 (i.e., core sections Y, Z, A to F) and a scattered light quantity observed by each of the optical elements 20 (i.e., optical elements Y, Z, A to F) fabricated by using these core sections 51, while FIG. 5B is a graph of a relationship between the Spc value of the surface of the replica of each of the substrates 21 (i.e., substrates Y, Z, A to F) and a scattered light quantity observed by each of the optical elements 20 (i.e., optical elements Y and Z, A to F) obtained from these substrates 21. As apparent from both the graphs, it is understood that the Spc value of the core section 51 or the like and scattered light quantity have a substantially linear relationship, and that as the Spc value becomes smaller, the scattered light quantity also becomes smaller. That is, the Spc value of the molding surface 51t of the core section 51 and the Spc value of the surface of a replica of the substrate 21 are the indicators in evaluating the scattered light quantity of the optical element 20 fabricated by utilizing the core section 51. That is, by controlling the molding surface 51t and the like of the core section 51 by utilizing the Spc value, the scattered light quantity of the optical element 20 can be controlled and the higher quality optical element 20 can be provided.

FIGS. 6A to 6D are graphs of a relationship between the surface roughness (Ra, Rq, Rz, and Rt) of each of the core sections 51 (i.e., core sections Y, Z, A to F), and the scattered light quantity observed by each of the optical elements 20 (i.e., optical elements Y, Z, A to F) fabricated by using these core sections 51. As apparent from the graphs, correlativity can be hardly found out between the surface roughness (Ra, Rq, Rz, and Rt) and the scattered light quantity, so we cannot say that as the surface roughness becomes smaller, the scattered light quantity becomes smaller. That is, even if the surface roughness of the core section 51 is used as an indicator, it is difficult to control the scattered light quantity of the optical element 20 obtained from this core section 51.

As apparent from Table 2 and the like, in the case of the optical element 20 fabricated by using the core section 51 having the molding surface 51t whose Spc value exceeds 100 [1/mm], the scattered light quantity was extremely large and therefore a sufficient performance (S/N ratio) could not be obtained. On the other hand, in the case of the optical element 20 fabricated by using the core section 51 having the molding surface 51t whose Spc value ranges 30 [1/mm] to 100 [1/mm], the scattered light quantity was small and therefore a sufficient performance (S/N ratio) could be obtained.

Note that, in the case of the optical element 20 fabricated by using the core section 51 having the molding surface 51t whose Spc value is on the order of 30 [1/mm], the scattered light quantity is significantly small. That is, it is considered that in the case of the optical element 20 fabricated by using the core section having a molding surface whose Spc value falls below 30 [1/mm], the adjustment of the angle (determination of the plasmon resonance angle) at which the surface to be irradiated IS is irradiated with the irradiation light LI is not easy. Moreover, for the core section 51 having the molding surface 51t whose Spc value is less than 30 [1/mm], the technical level required for machining was high and therefore the machining cost increased. Therefore, it is considered that the core section having a molding surface whose Spc value falls below 30 [1/mm] is not easy to be machined in terms of technique and/or cost.

In the foregoing, the present invention has been explained according to the embodiments, but the present invention is not limited to the above-described embodiments, and various modifications are possible. For example, in the above-described embodiments, the surface 21a of the optical element 20 on a side facing an object to be measured is formed from the molding surface 51t provided in the core section 51 of the fixed mold 41, but the surface 21a of the optical element 20 on a side facing an object to be measured may be formed from the molding surface 61t provided in the core section 61 of the movable mold 42. In this case, the Spc value of the molding surface 61t is desirably equal to or greater than 30 [1/mm] and equal to or less than 100 [1/mm].

In the above-described embodiments, the substrate 21 of the optical element 20 is assumed to be formed by injection molding of a thermoplastic resin, but the substrate 21 can also be fabricated by hot-press molding of a thermoplastic resin. Furthermore, the substrate 21 can also be fabricated by UV curing molding of a UV curable resin, and the substrate 21 can also be fabricated by heat-curing molding of a thermosetting resin. The substrate 21 of the optical element 20 can be accurately and stably mass-produced by injection molding or the like. In performing UV curing molding of a UV curable resin, a core section made of a UV light transmissive resin or glass is used, for example. As explained above, when a core section made of resin or glass is used, the Spc value of the molding surface of such a core section made of resin or glass is adapted to be equal to or greater than 30 [1/mm] and equal to or less than 100 [1/mm]. Moreover, the Spc value of the molding surface of such a core section made of resin or glass is preferably equal to or greater than 40 [1/mm] and equal to or less than 60 [1/mm].

The outer shape of the optical element 20 illustrated in FIG. 2A etc. is just illustrative, and can be appropriately changed in accordance with the specification of the measurement apparatus 70. The optical element 20 can also be fabricated not only from a resin but glass.

Figure 3:
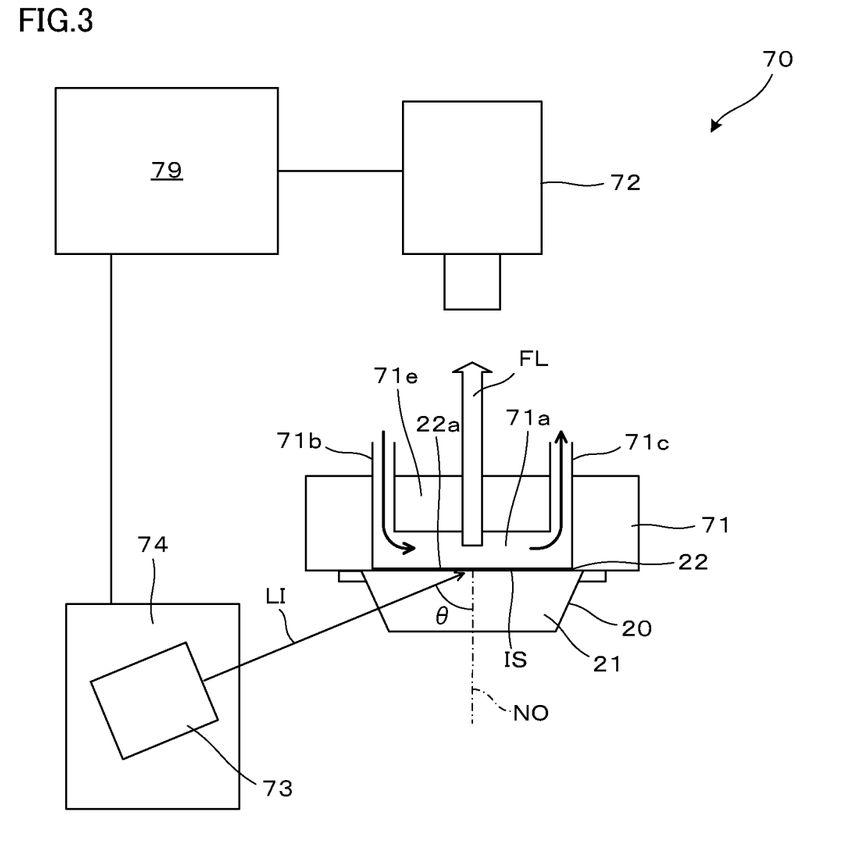
FIG. 3 is a conceptual diagram illustrating a measurement apparatus incorporating the optical element illustrated in FIG. 2.

Although the measurement apparatus 70 illustrated in FIG. 3 uses Surface Plasmon-field enhanced Fluorescence Spectroscopy, but the optical element 20 of the embodiment can be used in the applications requiring the suppression and/or control of the scattering light related to surface plasmon resonance, i.e., various sensors using surface plasmon resonance other than the Surface Plasmon-field enhanced Fluorescence Spectroscopy.

The invention claimed is:

1. A forming mold for a substrate of an optical element used for measurements utilizing surface plasmon, wherein an Spc value of a molding surface for transferring a shape onto a surface of the substrate on a side facing an object to be measured is equal to or less than 100 [1/mm].

2. The forming mold according to claim 1, wherein the Spc value of the molding surface is equal to or greater than 30 [1/mm].

3. The forming mold according to claim 1, wherein the Spc value of the molding surface is equal to or greater than 40 [1/mm] and equal to or less than 60 [1/mm].

4. The forming mold according to claim 1, wherein: the substrate is formed by either one of injection molding, hot-press molding, UV curing molding, and heat-curing molding; and includes a core section made of metal or resin which transfers a shape onto a surface of the substrate on a side facing an object to be measured, the core section being as an object in which Spc value is evaluated.

5. The forming mold according to claim 1, wherein the core section made of metal contains either one or more of a carbon steel, an aluminum alloy, a copper alloy, a cemented carbide, and a titanium alloy.

6. The forming mold according to claim 5, wherein the core section made of metal is the one obtained by applying nickel-P plating onto a surface of a body portion.

7. An optical element used for measurement utilizing surface plasmon, wherein an Spc value of a surface to be irradiated on a back side of a sensor face is equal to or less than 100 [1/mm].

8. The optical element according to claim 7, wherein the Spc value of the surface to be irradiated is equal to or greater than 28 [1/mm].

9. The optical element according to claim 7, comprising: an optically-transparent substrate; and a metal film which covers a surface of the substrate on a side facing an object to be measured to function as the surface to be irradiated, and has the sensor face on a front side.

10. The optical element according to claim 9, wherein the substrate is formed from a resin.

11. The optical element according to claim 10, wherein the substrate is either one of a thermoplastic resin, a UV curable resin, and a thermosetting resin.

12. The optical element according to claim 10, wherein the substrate is formed by molding using a forming mold.

13. The optical element according to claim 9, wherein the metal film is formed from either one of gold, silver, aluminum, platinum, copper, titanium, and chromium, or an alloy containing two or more thereof.

14. A method for producing an optical element used for measurement utilizing surface plasmon, wherein a substrate of the optical element is formed by using a forming mold, and an Spc value of a molding surface for transferring a shape onto a surface of the substrate on a side facing an object to be measured of the forming mold is equal to or greater than 30 [1/mm] and equal to or less than 100 [1/mm].

15. The method for producing an optical element according to claim 14, wherein the forming mold includes a core section made of metal which transfers a shape onto a surface of the substrate on a side facing an object to be measured, the core section being as an object in which an Spc value is evaluated, and the core section made of metal contains either one or more of a carbon steel, an aluminum alloy, a copper alloy, a cemented carbide, and a titanium alloy.

* * * * *